United States Patent [19]

Schmierer et al.

[11] Patent Number: 4,615,726
[45] Date of Patent: Oct. 7, 1986

[54] HERBICIDAL 1-ACYLIMIDAZOLINONES

[75] Inventors: Roland Schmierer, Gersthofen; Reinhard Handte, Gablingen; Hilmar Mildenberger, Kelkheim; Klaus Bauer, Rodgau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 682,795

[22] Filed: Dec. 18, 1984

[30] Foreign Application Priority Data

Dec. 20, 1983 [DE] Fed. Rep. of Germany ....... 3345901

[51] Int. Cl.$^4$ .................. A01N 43/84; C07D 401/04; C07D 233/70
[52] U.S. Cl. .......................................... 71/92; 544/82; 544/121; 544/128; 544/131; 544/139; 544/363; 544/364; 544/370; 546/15; 546/141; 546/142; 546/144; 546/153; 546/155; 546/156; 546/157; 546/167; 546/187; 546/193; 546/194; 546/205; 546/206; 546/210; 546/278; 548/301
[58] Field of Search ................ 548/301; 546/278, 187, 546/141, 205, 142, 206, 144, 193, 153, 194, 155, 210, 156, 157, 167, 15; 71/92; 544/128, 131, 139, 363, 364, 370, 121, 82

[56] References Cited

U.S. PATENT DOCUMENTS 4,188,487 2/1980 Los ..................................... 548/301

Primary Examiner—Richard A. Schwartz
Attorney, Agent, or Firm—Curtis, Morris & Safford

[57] ABSTRACT

Compounds of the formula

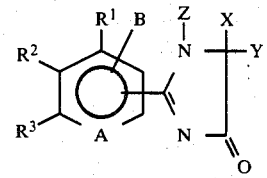

wherein A denotes N or $CR^4$, B denotes a carboxyl, carbo-(thio) ester, (substituted) carboxamide or carboxanilide, carbohydroxy(alkoxy)-amide, (substituted) carbohydrazide or (substituted) oxazoline group, X and Y denote, inter alia, alkyl or, together, spiroalkyl, Z denotes a carbo-(di)(thio) ester, carboxyl, (substituted) (thio)-carboxamide or -carboxanilide group or the radical of a ketone-acid or of a ketone-ester and $R^1$, $R^2$, $R^3$ and $R^4$ denote H or are identical or different and denote halogen, alkyl, alkoxy, alkoxycarbonyl, halogenoalkyl, $NO_2$, CN, (substituted) phenyl or phenoxy, or two of these radicals can form a $—CH=CH—CH=CH—$ group, are useful total or selective herbicides for application by the pre-emergence and, in some cases, the post-emergence method.

10 Claims, No Drawings

HERBICIDAL 1-ACYLIMIDAZOLINONES

It has already been disclosed that imidazolinones, such as are described, for example, in German Offenlegungsschriften DE-OS No. 2,833,274 and DE-OS No. 3,121,736, have herbicidal properties. However, the herbicidal action of the proposed compounds is frequently inadequate, or selectivity problems occur when the herbicidal action is appropriate. The existing need for solutions to problems where the disadvantages mentioned do not occur is fulfilled by the novel compounds of the general formula I, according to the invention.

The present invention relates to compounds of the general formula I

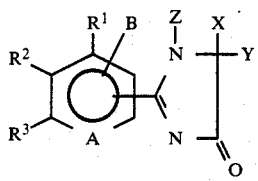

in which
A denotes N or C—$R^4$;
denotes

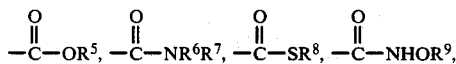

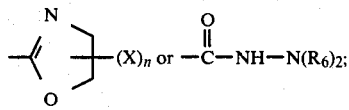

denotes $C_1$ to $C_4$-alkyl; and
Y denotes $C_1$–$C_6$-alkyl, $C_3$–$C_6$-cycloalkyl, $C_2$–$C_4$-alkenyl, $C_2$–$C_4$-alkinyl, phenyl or benzyl; or
X and Y, together with the carbon atom to which they are bonded, denote a $C_3$–$C_6$-spirocycloalkyl group which is optionally substituted by —$CH_3$;
Z denotes

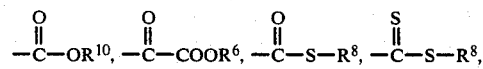

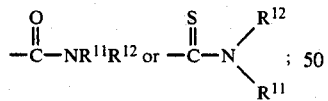

n denotes 0, 1 or 2;
$R^1$, $R^2$ $R^3$ and $R^4$ independently of one another denote hydrogen, and halogen, $C_1$–$C_4$-alkyl, $C_1$–$C_6$-alkoxy, $C_1$–$C_6$-alkoxycarbonyl, $C_1$- or $C_2$-halogenoalkyl, nitro, cyano, phenoxy or phenyl, which can optionally be substituted by $C_1$–$C_4$-alkoxy or halogen, it being possible for in each case two radicals $R^1$, $R^2$, $R^3$ or $R^4$ in the o-position relative to one another also together to form the grouping —CH=CH—CH=CH—;
$R^5$ denotes hydrogen, $C_1$–$C_{12}$-alkyl, which is optionally mono- or di-substituted, but preferably monosubstituted, by $C_1$–$C_4$-alkoxy, ($C_1$–$C_4$)-alkoxyethoxy, $C_3$–$C_6$-cycloalkyl, benzyloxy, phenyl, halogen, cyano, hydroxyl, oxiranyl, tetrahydrofuryl, ($C_1$–$C_4$)-alkylamino-($C_1$–$C_4$)-alkyl, ($C_1$–$C_4$)-alkylamino, ($C_1$–$C_4$)-dialkylamino, $C_1$–$C_4$-alkylthio, $C_1$–$C_4$-alkylsulfinyl, $C_1$–$C_4$-alkylsulfonyl, triazolyl or imidazolyl; $C_3$–$C_6$-alkenyl, $C_3$–$C_6$-halogenoalkenyl, $C_3$–$C_6$-cycloalkyl, $C_5$–$C_6$-cycloalkenyl, or $C_3$–$C_6$-alkinyl; benzyl, which can optionally be substituted in the benzene nucleus by chlorine or methyl; phenyl, which can optionally be substituted by up to two $C_1$–$C_4$-alkyl, nitro, halogen or methoxy groups; the group

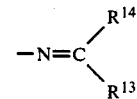

or a cation of an inorganic or organic base;
$R^6$ denotes hydrogen, $C_1$–$C_4$-alkyl or phenyl; and
$R^7$ denotes hydrogen, $C_1$–$C_6$-alkyl, which is optionally substituted by a hydroxyl group or a $C_1$–$C_3$-alkoxy group; $C_1$–$C_4$-alkylsulfonyl or halogeno-$C_1$–$C_4$-alkylsulfonyl; or $C_3$-alkenyl or $C_3$-alkinyl; or
$R^6$ and $R^7$, together with the nitrogen atom, denote a 5-membered or 6-membered ring in which one carbon atom can be replaced by oxygen or nitrogen and which is optionally substituted by up to two methyl groups;
$R^8$ denotes hydrogen, $C_1$–$C_6$-alkyl, phenyl, methylphenyl, halogenophenyl or a cation of an inorganic or organic base;
$R^9$ denotes hydrogen or $C_1$–$C_6$-alkyl;
$R^{10}$ denotes a radical having the meaning given for $R^5$, excluding hydrogen, alkylaminoalkyl or

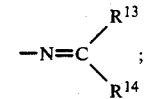

$R^{11}$ denotes hydrogen, $C_1$–$C_{14}$-alkyl, preferably $C_1$–$C_6$-alkyl, which can optionally be substituted by up to three halogen atoms or by a $C_1$–$C_4$-alkoxy, nitro, cyano or phenyl group, $C_3$–$C_6$-cycloalkyl, $C_3$–$C_6$-alkenyl, $C_3$–$C_6$-alkinyl, phenyl, which can optionally be substituted by up to two halogen, $C_1$–$C_4$-alkyl, trihalogenomethyl, nitro, $C_1$–$C_4$-alkoxy or cyano groups, amino, $C_1$–$C_4$-alkylamino, anilino, $C_1$–$C_4$-dialkylamino, $C_1$–$C_6$-alkylcarbonyl, trihalogenoacetyl, benzoyl, halogenobenzoyl, methylbenzoyl, phenylsulfonyl, halogenophenylsulfonyl or alkylphenylsulfonyl; and
$R^{12}$ denotes a radical having the meaning given for $R^6$; or
$R^{11}$ and $R^{12}$, together with the nitrogen atom, denote a 5-membered or 6-membered ring, in which one carbon atom can be replaced by oxygen or nitrogen and which is optionally substituted by up to two methyl groups; and
$R^{13}$ and $R^{14}$ independently of one another denote hydrogen, $C_1$–$C_4$-alkyl, $C_1$–$C_4$-alkoxyalkyl, $C_3$–$C_6$-cycloalkyl or phenyl, or together with the carbon atom to which they are bonded denote a $C_5$- or $C_6$-cycloalkyl group;
and their optical isomers (if X≠Y), acid addition compounds and N-oxides (where A represents N).

Preferred possible cations in the R5- and/or R8-position are $Na^+$, $K^+$, $\frac{1}{2} Mg^{2+}$, $\frac{1}{2} Ca^{2+}$, $\frac{1}{2} Cu^{2+}$, $\frac{1}{2} Fe^{2+}$, $\frac{1}{2} Zn^{2+}$, $NH_4^+$ and ammonium with organic substituents, such as $^{30}NH(C_2H_5)_3$, $^{30}NH_3CH_2CH_2OH$ or $^+NH(CH_2CH_2OH)_3$. Acid addition compounds (where A=N) are formed with strong acids, such as HCl or $H_2SO_4$.

The compounds of the formula I according to the invention are obtained by acylating the compounds of the formula II

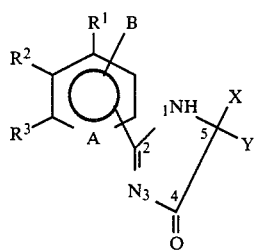

in the 1-position on the imidazoline ring.

The compounds of the formula II are known per se or can be prepared by known processes, such as are described in German Offenlegungsschrift No. 2,833,274 and German Offenlegungsschrift No. 3,121,736. If the molecule contains other acylatable groupings, these can first be protected (for example as esters or benzyl ethers) and, after the acylation, converted into the compounds of the formula I by suitable methods (for example hydrolysis, hydrogenation, transesterification).

Suitable acylating agents are, for example, acyl halides in the presence of bases; and isocyanates or isothiocyanates. It is also possible to prepare reactive intermediates (such as, for example, xanthogenates or chlorocarbonyl compounds) from the compounds II, which can then be further reacted, for example by alkylation, alcoholysis, aminolysis or hydrazinolysis, to give the compounds according to the invention by processes which are known per se (Houben-Weyl IX page 823 et seq.). The reaction temperatures are not critical for the acylation reactions. The reactions are usually carried out at temperatures from $-10°$ C. to $+140°$ C., advantageously at $0°$ C. to $100°$ C., in the presence of an inert solvent. Suitable bases for the reaction of the acyl halides are both inorganic bases, such as sodium carbonate, and organic bases, such as, for example, pyridine or triethylamine. The addition of catalytic amounts of a tertiary base in general has an advantageous effect on the reactions with the isocyanates and isothiocyanates.

The compounds of the formula II are tautomeric, so that the compounds according to the invention can also exist in one of the two forms Ia/Ib or as a mixture of Ia and Ib.

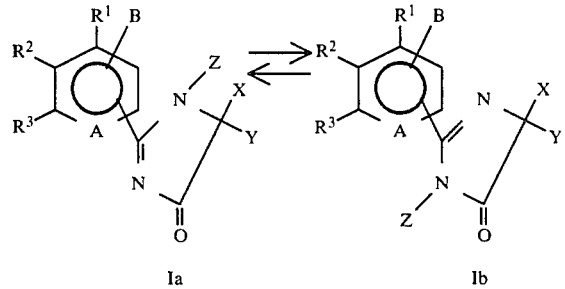

If unsymmetrically substituted phthalic acid derivatives are used for the synthesis of the phenyl compounds ($A=CR^4$), isomer mixtures of the compounds of the formula II are possible (cf. German Offenlegungsschrift No. 2,833,274). The compounds according to the invention can then likewise exist as a mixture of the two position isomers.

The present compounds according to the invention have an excellent herbicidal activity against a wide spectrum of economically important monocotyledon and dicotyledon harmful plants. The active substances also have a good action on perennial root-propagated weeds which are difficult to combat. It is irrelevant here whether the substances are applied by pre-sowing, pre-emergence or post-emergence spraying. If the compounds according to the invention are applied to the soil surface before germination, emergence of the seedlings is not completely prevented. The weeds grow to the cotyledon stage, but their growth then stops and, finally, they die completely after three weeks.

With some compounds, a stop in growth likewise occurs very rapidly after treatment when these compounds are applied to the green parts of plants by the post-emergence method, and the weeds remain in the growth stage in which they existed at the time of application, or they die completely after a certain time, so that competition by weeds, which is harmful to the crop plant, can in this may be eliminated very early and permanently. Although the compounds according to the invention have an excellent herbicidal activity against monocotyledon and dicotyledon weeds, plants in economically important crops such as, for example, wheat, barley, rye, rice, corn, sugarbeet, cotton and soybean, are in some cases damaged only insignificantly, if at all. Some of the substances according to the invention thus have a considerably improved selectivity in crop plants in comparison with the prior art. For these reasons, they are particularly suitable for combating undesirable plant growth in agricultural crop plantations.

Moreover, the compounds according to the invention have growth-regulating properties in crop plants. They have a regulating effect on the endogenous metabolism of the plant and can thus be used to facilitate harvesting, such as, for example, by inducing desiccation, abscission and growth compression. They are furthermore also suitable for general control and inhibition of undesirable vegetative growth, without thereby destroying the plants. An inhibition of vegetative growth is of great importance in many monocotyledon and dicotyledon crops, since lodging can thereby be reduced or completely prevented.

The agents according to the invention can be applied as wettable powders, emulsifiable concentrates, solutions which can be sprayed, dusts, dressing agents, dispersions, granules or microgranules in the usual formulations.

Wettable powders are products which are uniformly dispersible in water and which, in addition to the active substance, and apart from a diluent or inert substance, if appropriate, also contain wetting agents, for example polyoxyethylated alkyl phenols, polyoxyethylated fatty alcohols or alkyl- or alkylphenyl-sulfonates, and dispersing agents, for example sodium lignin-sulfonate, sodium 2,2'-dinaphthylmethane-6,6'-disulfonate, sodium dibutylnaphthalenesulfonate or sodium oleyl-methyltauride. The products are prepared in the usual manner, for example by grinding and mixing the components.

Emulsifiable concentrates can be prepared, for example, by dissolving the active substance in an inert organic solvent, for example butanol, cyclohexanone, dimethylformamide, xylene or higher-boiling aromatics or hydrocarbons, with the addition of one or more emulsifiers. In the case of liquid active substances, all or some of the solvent content can also be omitted. Examples of emulsifiers which can be used are: calcium alkylarylsulfonates, such as Ca dodecyl-benzenesulfonate, or non-ionic emulsifiers, such as fatty acid polyglycol esters, alkyl-aryl polyglycol ethers, fatty alcohol polyglycol ethers, propylene oxide/ethylene oxide condensates, fatty alcohol/propylene oxide/ethylene oxide condensates, alkyl polyglycol ethers, sorbitan fatty acid esters, polyoxyethylene sorbitan fatty acid esters or polyoxyethylene sorbitol esters.

Dusts can be obtained by grinding the active substance with finely divided, solid substances, for example talc or natural clays, such as kaolin, bentonite, pyrophillite or diatomaceous earth.

Granules can be prepared either by spraying the active substance onto a granular inert adsorbent material, or by applying active substance concentrates to the surface of carriers, such as sand or kaolinites, or of granular inert material, by means of binders, for example, polyvinyl alcohol, sodium polyacrylate or mineral oils. Suitable active substances can also be granulated in the usual manner for the preparation of fertilizer granules, if appropriate as a mixture with fertilizers.

The active substance concentration in wettable powders is, for example, about 10 to 90% by weight, the remainder to make up to 100% by weight consisting of the usual formulation constituents. The active substance concentration in emulsifiable concentrates can be about 10 to 80% by weight. Dust-like formulations usually contain 5 to 20% by weight of active substance, and solutions which can be sprayed usually contain about 2 to 20% by weight. The active substance content of granules depends partly on whether the active compound is in liquid or solid form and on the granulation auxiliaries, fillers and the like used.

The active substance formulations mentioned also contain, if appropriate, the particular customary tackifying agents, wetting agents, dispersing agents, emulsifiers, penetration agents, solvents, fillers or carriers.

For application, the concentrates in the commercially available form are diluted, if appropriate, in the customary manner, for example by means of water in the case of wettable powders, emulsifiable concentrates, dispersions and in some cases also microgranules. Dust-like and granular formulations and solutions which can be sprayed are usually not further diluted with additional inert substances before application.

The application amount required varies according to the external conditions, such as temperature, humidity and the like. It can vary within wide limits, for example between 0.005 and 10.0 kg/ha or more of active substance, but is preferably between 0.05 and 5 kg/ha.

Mixures or mixed formulations with other active substances, such as, for example, insecticides, acaricides, herbicides, fertilizers, growth regulators or fungicides, are also possible, where appropriate.

Some formulation examples are described below:

A dust is obtained by mixing 10 parts by weight of active substance and 90 parts by weight of talc or inert substance and comminuting the mixture in an impact mill.

A wettable powder which is readily dispersible in water is obtained by mixing 25 parts by weight of active substance, 64 parts by weight of kaolin-containing quartz, as the inert substance, 10 parts by weight of potassium lignin-sulfonate and 1 part by weight of sodium oleyl-methyl-tauride, as the wetting agent and dispersing agent, and grinding the mixture in a pinned disk mill.

A dispersion concentrate which is readily dispersible in water is obtained by mixing 20 parts by weight of active substance with 6 parts by weight of alkylphenol polyglycol ether (Triton X 207), 3 parts by weight of isotridecanol polyglycol ether (8 mol of ethylene oxide) and 71 parts by weight of paraffinic mineral oil (boiling range for example about 255° to about 377° C.) and grinding the mixture to a fineness of less then 5 microns in a ball mill.

An emulsifiable concentrate is obtained from 15 parts by weight of active substance, 75 parts by weight of cyclohexanone, as the solvent, and 10 parts by weight of oxyethylated nonylphenol (10 mol of ethylene oxide), as the emulsifier.

The following examples serve to further illustrate the invention:

A. PREPARATION EXAMPLES

EXAMPLE 1

2-(2-Ethoxycarbonylphenyl)-5-isopropyl-1-methoxycarbonyl-5-methyl-4-oxo-2-imidazoline 8 g (0.028 mole) of 2-(2-ethoxycarbonylphenyl)-5-isopropyl-5-methyl-4-oxo-2-imidazoline are dissolved in 30 ml of absolute pyridine, and 5.3 g (0.056 mole) of methyl chloroformate are added at room temperature. After 1 hour, the mixture is poured onto ice and extracted twice with 100 ml of toluene each time and the organic phase is washed twice with water, dried and evaporated. 8.7 g (90% of theory) of 2-(2-ethoxycarbonylphenyl)-5-isopropyl-1-methoxycarbonyl-5-methyl-4-oxo-2-imidazoline are obtained as a colorless oil.

$^1$H-NMR (60 MHz, CDCl$_3$) $\delta$=0.98, 1.09 (2d, J=7 Hz, —CH—(CH3)$_2$, each of 3H); 1.28 (t, J=7 Hz, —OCH$_2$—CH$_3$, 3H); 1.43 (s, —CH$_3$, 3H); 2.17 (h, J=7 Hz, CH—CH$_3$)$_2$, 1H); 3.63 (s, OCH$_3$, 3H); 4.25 (q, J=7 Hz, O—CH$_2$—, 2H); and 7.3–8.0 ppm (m, 4H, phenyl).

EXAMPLE 2

2-(2-Ethoxycarbonylphenyl)-1-N-ethylcarbamoyl-5-isopropyl-5-methyl-4-oxo-2-imidazoline 9 g (0.031 mole) of 2-(2-ethoxycarbonylphenyl)-5-isopropyl-5-methyl-4-oxo-2-imidazoline are dissolved in 30 ml of absolute methylene chloride, and 2.7 g (0.038 mole) of ethyl isocyanate and 0.5 ml of DBU are added at room temperature. After a reaction time of 1 hour, the mixture is poured onto ice and the organic phase is washed twice with water, dried and evaporated. 11.0 g (98% of theory) of 2-(2-ethoxycarbonylphenyl)-1-N-ethylcarbamoyl-5-isopropyl-5-methyl-4-oxo-2-imidazoline are obtained as colorless tablets of melting point 85°–87° C.

EXAMPLE 3

2-(2-Butoxycarbonylphenyl)-1-N',N'-dimethylcarbazoyl-5-isopropyl-5-methyl-4-oxo-2-imidazoline A mixture of 10 g (0.032 mole) of 2-(2-butoxycarbonylphenyl)-5-isopropyl-5-methyl-4-oxo-2-imidazoline, 3 g (0.038 mole) of pyridine and 30 ml of methylene chloride is added dropwise to a solution of 3.85 g (0.039 mole) of phosgene in 25 ml of chlorobenzene at room temperature. The mixture is stirred at room temperature for 1 hour and cooled to 5° C., and 4.4 g (0.073 mole) of N,N-dimethylhydrazine are added dropwise at this temperature. The mixture is allowed to warm to room temperature and is poured onto water, and the organic phase is washed twice more with 100 ml of water each time, dried and evaporated. After purification by chromatography (silica gel, eluant: petroleum ether/ethyl acetate 7:3), 7.8 g (61% of theory) of 2-(2-butoxycarbonylphenyl)-1-N',N'-dimethylcarbazoyl-5-isopropyl-5-methyl-4-ozo-2-imidazoline are obtained as a pale yellow oil.

$^1$H-NMR (60 MHz, CDCl$_3$) $\delta$=0.97, 1.10 (2dd, J=7 Hz, each of 3H, —CH(CH$_3$)$_2$); 1.43 (s, 3H, CH$_3$): 0.85–2.3 (sh, 8H, CH$_2$—C$\underline{H}$$_2$—CH$_3$, —CH(CH$_3$)$_2$); 2.53 (s, 6H, N(CH$_3$)$_2$); 4.17 (t, J=7 Hz, 2H, —OCH$_2$); 7.3–8.2 ppm (m, 4H, phenyl) and 8.90 ppm (s, 1H, NH).

The examples of Table 1 are prepared in an analogous manner.

TABLE 1
Compounds of the general formula I

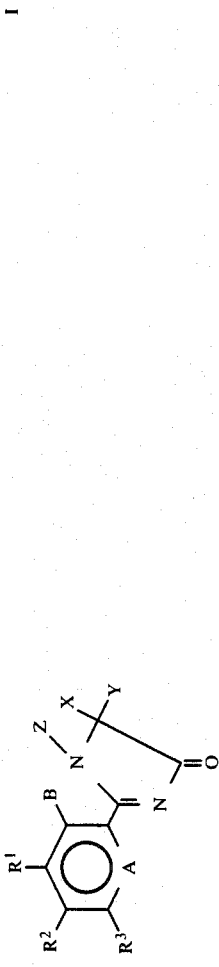

| Example No. | R¹ | R² | R³ | A | B | X | Y | Z | Melting point [°C] |
|---|---|---|---|---|---|---|---|---|---|
| 4 | H | H | H | CH | $CONH_2$ | $CH_3$ | $CH_3$ | $-\overset{S}{\underset{\|}{C}}-SCH_3$ | Oil |
| 5 | " | " | " | " | COOH | " | " | $-\overset{O}{\underset{\|}{C}}-NH-\!\!\!\bigcirc\!\!\!-CF_3$ | " |
| 6 | " | " | " | N | $COOCH_3$ | " | $C_2H_5$ | $-\overset{O}{\underset{\|}{C}}-NH-n-C_8H_{17}$ | " |
| 7 | " | " | " | " | " | " | $CH(CH_3)_2$ | $-\overset{O}{\underset{\|}{C}}-NH-NHCH_3$ | " |
| 8 | " | " | " | " | " | " | " | $-\overset{O}{\underset{\|}{C}}-NH-CH_3$ | 91–3 |
| 9 | " | " | " | CH | " | " | " | $-\overset{O}{\underset{\|}{C}}-NH-CH_3$ | resin |
| 10 | " | " | " | " | " | " | " | $-\overset{O}{\underset{\|}{C}}-NH-C_2H_5$ | oil |
| 11 | " | " | " | " | " | " | " | $-\overset{S}{\underset{\|}{C}}-NH-C_2H_5$ | |
| 12 | " | " | " | " | " | " | " | $-\overset{O}{\underset{\|}{C}}-NH-CH_2-CH=CH_2$ | |

TABLE 1-continued

Compounds of the general formula I

| Example No. | R¹ | R² | R³ | A | B | X | Y | Z | Melting point [°C.] |
|---|---|---|---|---|---|---|---|---|---|
| 13 | " | " | " | " | " | " | " | $\underset{\text{O}}{\overset{\parallel}{-\text{C}}}-\text{NH}-\text{C}_4\text{H}_9$ | " |
| 14 | " | " | " | " | " | " | " | $\underset{\text{O}}{\overset{\parallel}{-\text{C}}}-\text{N}(\text{CH}_3)_2$ | " |
| 15 | " | " | " | " | " | " | " | -C(=O)-N(CH₃)-C₆H₅ | " |
| 16* | F | " | " | " | " | " | " | -C(=O)-NH-C₆H₄-Cl | " |
| 17* | " | " | Cl | " | " | " | " | 2,6-dimethylmorpholino carbonyl | " |
| 18* | " | " | CH₃ | " | " | " | " | $\underset{\text{O}}{\overset{\parallel}{-\text{C}}}-\text{NH}_2$ | resin |
| 19* | " | " | COOCH₃ | " | " | " | " | " | oil |

TABLE 1-continued
Compounds of the general formula I
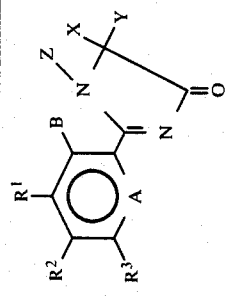
| Example No. | $R^1$ | $R^2$ | $R^3$ | A | B | X | Y | Z | Melting point [°C] |
|---|---|---|---|---|---|---|---|---|---|
| 20 | Cl | Cl | Cl | CCl | " | " | " | —C(=O)—NH—CH$_3$ | " |
| 21 | H | H | H | CH | " | " | " | —C(=O)—SNa | resin |
| 22 | " | " | " | " | " | " | " | —C(=O)—S—C$_2$H$_5$ | oil |
| 23 | " | " | " | " | " | " | " | —C(=O)—OCH$_3$ | " |
| 24 | " | " | " | " | " | " | " | —C(=O)—O—nC$_4$H$_9$ | " |
| 25 | " | " | " | " | " | " | " | —C(=O)—NH—NH$_2$ | " |
| 26 | " | " | " | " | " | " | " | —C(=O)—NH—C(=O)—C$_6$H$_5$ | " |
| 27 | " | " | " | " | COOC$_2$H$_5$ | " | —CH(CH$_3$)$_2$ | —C(=O)—NH—CH$_3$ | 90-2 |
| 28 | " | " | " | " | " | " | " | —C(=O)—OC$_2$H$_5$ | oil |

TABLE 1-continued
Compounds of the general formula 1
| Example No. | R¹ | R² | R³ | A | B | X | Y | Z | Melting point [°C.] |
|---|---|---|---|---|---|---|---|---|---|
| 29 | " | " | " | " | " | " | " | —C(=O)—O—phenyl | " |
| 30 | " | " | " | " | COOnC₄H₉ | " | " | —C(=O)—NH—CH₃ | 73-5 |
| 31 | " | " | " | " | " | " | " | —C(=O)—NHC₂H₅ | oil |
| 32 | " | " | " | " | " | " | " | —C(=O)—NH—cyclohexyl | " |
| 33 | " | " | " | " | " | " | " | —C(=O)—NH—SO₂—(2-Cl-phenyl) | resin |
| 34 | " | " | " | " | morpholinocarbonyl | " | cyclopropyl | —C(=S)—NH₂ | oil |
| 35 | " | " | " | " | —C(=O)—S—nC₄H₉ | " | —CH₂CH(CH₃)₂ | —C(=O)—O—CH₂—phenyl | " |

TABLE 1-continued

Compounds of the general formula I $$\text{R}^1\text{-C}_6\text{H}_2(\text{R}^2)(\text{R}^3)(\text{B})-\text{C}(=\text{N}-\text{N}(\text{Z})-\text{C}(\text{X})(\text{Y})-\text{C}(=\text{O})-)$$

| Example No. | $R^1$ | $R^2$ | $R^3$ | A | B | X | Y | Z | Melting point [°C.] |
|---|---|---|---|---|---|---|---|---|---|
| 36* | $NO_2$ | " | " | " | " | " | " | $-\overset{O}{\underset{\|}{C}}-NH-CH_3$ | |
| 37* | H | $CH_3$ | " | " | $-COO(CH_2)_2-OCH_3$ | $C_2H_5$ | $C_2H_5$ | $-\overset{O}{\underset{\|}{C}}-N(C_2H_5)_2$ | |
| 38 | " | " | " | " | $-COO(CH_2)_2-Cl$ | " | " | $-\overset{O}{\underset{\|}{C}}-NH-\overset{O}{\underset{\|}{C}}-CCl_3$ | |
| 39 | " | $-CH=CH-CH=CH-$ | | " | $-COONa$ | $CH_3$ | $-CH(CH_3)_2$ | $-\overset{O}{\underset{\|}{C}}-NHCH_3$ | |
| 40 | " | " | " | " | $-COO(CH_2)_2-N(CH_3)_2$ | " | " | $-\overset{O}{\underset{\|}{C}}-SCH_3$ | |
| 41 | " | " | " | N | $-COOH$ | " | " | $-\overset{O}{\underset{\|}{C}}-N(CH_3)_2$ | |
| 42 | " | " | " | " | $-COOCH_2CH=CH_2$ | $C_2H_5$ | $C_2H_5$ | $-\overset{O}{\underset{\|}{S}}-C_6H_5$ | hydro-chloride |
| 43* | " | H | CN | CH | $-COO-C_6H_{11}$ | " | $CH(CH_3)_2$ | $-\overset{O}{\underset{\|}{C}}-NHCH_2CH_2OCH_3$ | |

TABLE 1-continued

Compounds of the general formula 1

| Example No. | R¹ | R² | R³ | A | B | X | Y | Z | Melting point [°C.] |
|---|---|---|---|---|---|---|---|---|---|
| 44 | " | " | H | " | —CONHOCH₃ | —CHCH₂CH₂CH₂— <br> \|<br>CH₃ | —CHCH₂CH₂CH₂— | 3,4-Cl₂-C₆H₃-N(CH₃)-CO— | |
| 45 | " | " | " | " | (2-methyl-4,5-dihydro-oxazole) | " | " | —C(=O)—S—C₃H₇ | |
| 46 | " | " | " | " | COO—N=C(CH₃)(CH₃) | " | " | —C(=O)—O—CH₂—CH₂—Cl | |
| 47 | " | " | " | " | COOCH₃ | CH₃ | C₂H₅ | —CONHCH₃ | 97–101 |
| 48 | " | " | " | " | COOC₂H₅ | " | " | " | oil |
| 49 | " | " | " | " | " | " | " | —CONHC₂H₅ | " |
| 50 | " | " | " | N | COOCH₃ | " | CH(CH₃)₂ | " | " |
| 51 | " | " | " | " | " | " | " | —COOCH₃ | " |
| 52 | " | —CH=CH—CH=CH— | " | CH | " | " | " | —CONHCH₃ | 163–41 |
| 53 | " | " | H | " | " | " | " | —CONH—CH(CH₃)₂ | oil |
| 54 | " | " | " | " | " | " | " | cyclopropyl-CO— | 90–5 |

TABLE 1-continued

Compounds of the general formula I

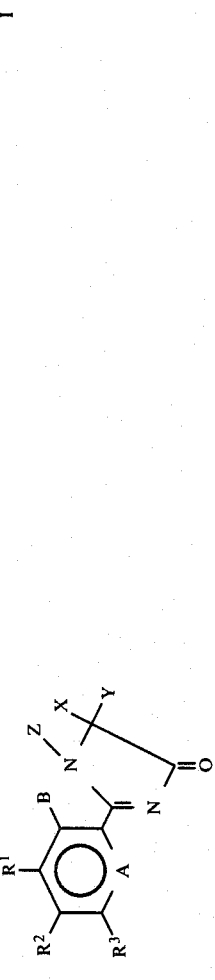

| Example No. | R¹ | R² | R³ | A | B | X | Y | Z | Melting point [°C.] |
|---|---|---|---|---|---|---|---|---|---|
| 55 | " | " | " | " | " | " | " | piperidine-N—CO— | oil |
| 56 | " | " | " | " | " | " | " | 2,6-dimethylmorpholine-N—CO— | " |
| 57 | " | " | " | " | " | " | " | —CONH—C₆H₄Cl | " |
| 58 | " | " | " | " | " | " | " | —CONHC(CH₃)CH(CH₃)₂ CN | 68-74 |
| 59 | " | " | " | " | COOC₂H₅ | " | " | —COCOOCH₃ | 92-3 |
| 60 | " | " | " | " | COO—n-C₄H₉ | " | " | —CONH—n-C₄H₉ | oil |
| 61* | " | CH₃ | " | " | COOCH₃ | " | " | —CONH₂ | " |
| 62* | " | " | " | " | " | " | " | —CONHCH₃ | " |
| 63* | " | " | " | " | " | " | " | —CONHC₂H₅ | " |
| 64* | " | " | " | " | " | " | " | —COCOOCH₃ | " |
| 65* | " | " | " | " | " | " | " | —COOCH₃ | " |
| 66* | " | " | " | " | " | " | " | —COOPhenyl | " |
| 67* | " | " | " | " | " | " | " | —COS—n-C₆H₁₃ | " |
| 68* | " | " | " | " | " | " | " | —CONH—N(CH₃)₂ | " |
| 69* | " | " | " | " | " | " | " | —CONH—CH(CH₃)₂ | " |

TABLE 1-continued

Compounds of the general formula I

| Example No. | R$^1$ | R$^2$ | R$^3$ | A | B | X | Y | Z | Melting point [°C] |
|---|---|---|---|---|---|---|---|---|---|
| 70* | " | " | " | " | " | " | " | —CONH—⟨C$_6$H$_4$⟩—Cl | " |
| 71 | " | " | " | " | " | " | CH(CH$_3$)C$_2$H$_5$ | CONHCH$_3$ | " |
| 72 | " | Cl | Cl | " | " | " | CH(CH$_3$)$_2$ | " | " |
| 73* | " | H | H | CCH$_3$ | COOCH$_2$—S—CH$_3$ | " | " | " | " |
| 74 | —CH=CH—CH=CH— | | | N | COOCH$_3$ | " | " | " | " |
| 75 | " | " | " | " | " | " | " | " | " |
| 76 | " | " | " | " | COOH | " | " | COOCH$_3$ | " |
| 77 | " | H | H | " | COO$^-$H$_3$N$^+$CH(CH$_3$)$_2$ | " | " | CONHCH$_3$ | " |
| 78 | " | H | H | " | | " | " | " | " |

*mixed with the compound which is a position isomer

B. BIOLOGICAL EXAMPLES

Test for herbicidal action

The damage to the weeds and the tolerance by the crop plants was rated on a scale of 0–5.
In this scale,
0 = no action (damage)
1 = 0–20% action
2 = 20–40% action
3 = 40–60% action
4 = 60–80% action
5 = 80–100% action

1. Action against weeds

Seeds or pieces of rhizome from monocotyledon and dicotyledon weeds were placed in loam soil in plastic pots ($\phi$ 9 cm) and covered with soil. The compounds according to the invention, formulated as wettable powders or as emulsion concentrates, were applied to the surface of the soil in the form of aqueous suspension or emulsions. The amount of water applied per pot thereby corresponded, when converted, to 600 l/ha. After the treatment, the experimental pots were placed in a greenhouse and the experimental plants were cultivated under good growing conditions (temperature: 23 + 1° C.; relative atmospheric humidity: 60–80%). After about 3 weeks, the damage to the plants was rated visually. Untreated controls were used here for comparison.

The compounds according to the invention exhibit a herbicidal activity, which is in some cases excellent, against economically important monocotyledon and dicotyledon harmful plants.

TABLE 2

| Example No. | Activity in the pre-emergence method against | | | |
|---|---|---|---|---|
| | ALM | POA | AMR | SIA |
| 1 | 5/5 | 5/3 | 5/5/5 | 5/5 |
| 2 | 5/5 | 5 | 5/5/5 | 5/4 |
| 3 | 5/5 | 5 | 5/5/5 | 5/4 |
| 8 | 5/5/5 | 5/5/5 | 5/5/5 | 5/5/5 |
| 9 | 5/5/4 | 5/5 | 5/5/4 | 5/5/4 |
| 10 | 5/5 | 5/5 | 5/5/5 | 5/5 |
| 15 | 5 | 4 | 5 | 5 |
| 22 | 5/5 | 3/3 | 5/5 | 5/5 |
| 23 | 5/5 | 5/5 | 5/5/5 | 5/5 |
| 24 | 5/5/4 | 5/5 | 5/5/4 | 5/5 |
| 27 | 5/5 | 5 | 5/5/5 | 5/5 |
| 28 | 5/5 | 5 | 5/5/5 | 5/5 |
| 29 | 5/5 | 4/3 | 5/5/5 | 5/4 |
| 30 | 5 | 5 | 5/5 | 5/5 |
| 31 | 5/4 | 5 | 5/5 | 5/4 |
| 32 | 4 | | 5 | 4 |
| 33 | 5 | 4 | 5/5 | 5/5 |
| 47 | 5/5 | 5/5 | 5/4 | 5/4 |
| 48 | 4 | 4 | 5/5 | 5/5 |
| 49 | 4/4 | 4 | 5/5 | 5/5 |
| 50 | 5/5/5 | 5/5/5 | 5/5/5 | 5/5/5 |
| 51 | 5/5/5 | 5/5/5 | 5/5/5 | 5/5/5 |
| 52 | 5 | | 4/4 | 5/4 |
| 53 | 5/5 | 5/5 | 5/5/4 | 5/5/4 |
| 55 | 5 | 4 | 5 | 5 |
| 56 | 4 | 4 | 5/4 | 4 |
| 57 | 5/5 | 5/5 | 5/5/5 | 5/5/4 |
| 58 | 5/5 | 5/5/4 | 5/5 | 5/5 |
| 59 | 5/5 | 5/5 | 5/5 | 5/5 |
| 60 | 5/4 | 4 | 5/5/5 | 5/4 |
| 61 | 5/5 | 5/5 | 5/5/4 | 5/5 |
| 62 | 5/5/5 | 5/4 | 5/4 | 5/5/4 |
| 63 | 5/5/5 | 5 | 5/4 | 5/5 |
| 64 | 5/5/5 | 5/4 | 5/4 | 5/5/4 |
| 65 | 5/5/5 | 5/4 | 5/4 | 5/5 |
| 66 | 5/5/5 | 5/4 | 5 | 5/5 |

TABLE 2-continued

| Example No. | Activity in the pre-emergence method against | | | |
|---|---|---|---|---|
| | LOM | ECG | STM | SIA |
| 68 | 4 | 4 | 5 | 5 |
| 69 | 4 | | 4 | 5 |
| 70 | 5 | 4 | 5 | 5 |

Various weeds were grown in pots in a greenhouse to the 3 to 6 leaf stage in a similar manner, and were then treated with the compounds according to the invention (formulated as wettable powders) by the post-emergence method. 4 weeks later, the experimental plants were rated visually in comparison with untreated control plants, by estimating the damage.

The compounds according to the invention also proved to have a good action in this experiment:

TABLE 3

| Example No. | Activity in the post-emergence method against | | | |
|---|---|---|---|---|
| | ALM | POA | AMR | SIA |
| 1 | 5 | | | 5/4 |
| 3 | | | 5 | 4 |
| 8 | 5/5 | 5/5/4 | 5/4 | 5/5 |
| 9 | 4 | 4 | 5 | 4 |
| 10 | | | | 5/4 |
| 22 | | | | 5 |
| 23 | | | | 5/4 |
| 24 | | | | 4 |
| 27 | 4 | | | 4 |
| 28 | | | 5 | |
| 29 | 4 | | | 4 |
| 47 | | 3 | 5 | 4 |
| 50 | 5/5 | 5/5/4 | 5/5 | 5/5/4 |
| 51 | 5/5 | 5/5/5 | 5/5/4 | 5/5/5 |
| 57 | | | 5 | 5 |
| 58 | 4 | | 5/4 | 5/5 |
| 59 | 5 | | | 5/5/4 |
| 62 | 5/4 | | | 5/4/4 |
| 63 | 5 | | | 5/5 |
| 64 | 5/4 | | | 5/5/4 |
| 65 | 5/4 | | 4 | 5/5/4 |
| 66 | 4/4 | 3 | 3 | 5/4 |
| 68 | 5/4 | | 4 | 5/5/4 |
| 69 | 5/4 | | 4 | 5/5/4 |
| 70 | 5/4 | | 4 | 5/5/4 |

Legend:
Test plants:
ALM = Alopecurus myosuroides
POA = Poa annua
AMR = Amaranthus retroflexus
SIA = Sinapis alba
LOM = Lolium multiflorum
ECG = Echinochloa crus-galli
STM = Stellaria media
1 figure = dosage of 2.4 kg/ha, for example 5
2 figures = dosages of 2.4–0.6 kg/ha, for example 5/4
3 figures = dosages of 2.4–0.6–0.15 kg/ha, for example 5/4/3

We claim:

1. A compound of the formula I

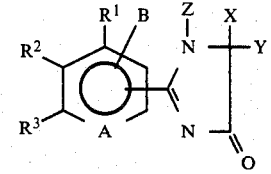

in which
A is N or C—$R^4$;
B is

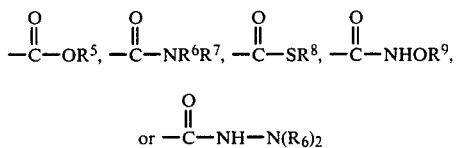

or $-\overset{O}{\underset{\|}{C}}-NH-N(R_6)_2$

X is $C_1$ to $C_4$-alkyl; and

Y is $C_1$-$C_6$-alkyl, $C_3$-$C_6$-cycloalkyl, $C_2$-$C_4$-alkenyl, $C_2$-$C_4$-alkinyl, phenyl or benzyl; or X and Y, together with the carbon atom to which they are bonded, form a $C_3$-$C_6$-spirocycloalkyl group which is unsubstituted or substituted by —$CH_3$;

Z is

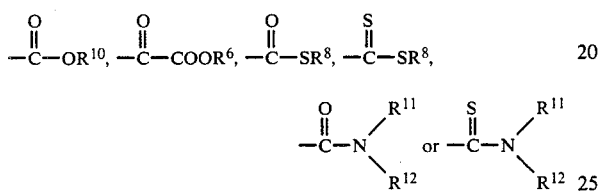

n is 0, 1 or 2;

$R^1$, $R^2$, $R^3$ and $R^4$ independently of one another are hydrogen, halogen, $C_1$-$C_4$-alkyl, $C_1$-$C_6$-alkoxy, $C_1$-$C_6$-alkoxycarbonyl, $C_1$- or $C_2$-halogenoalkyl, nitro, cyano, phenoxy or phenyl, which is unsubstituted or substituted by $C_1$-$C_4$-alkoxy or halogen, it being possible for in each case two $R^1$, $R^2$, $R^3$ or $R^4$ radicals, ortho to each to form the grouping —CH=CH—CH=CH—;

$R^5$ is hydrogen, $C_1$-$C_{12}$-alkyl, which is unsubstituted or mono- or di substituted by $C_1$-$C_4$-alkoxy, $(C_1$-$C_4)$-alkoxyethoxy, $C_3$-$C_6$-cycloalkyl, benzyloxy, phenyl, halogen, cyano, hydroxyl, $(C_1$-$C_4)$-alkylamino-$(C_1$-$C_4)$-alkyl, $(C_1$-$C_4)$-alkylamino, $(C_1$-$C_4)$-dialkylamino, $C_1$-$C_4$-alkylthio, $C_1$-$C_4$-alkylsulfinyl, $C_1$-$C_4$-alkylsulfonyl; $C_3$-$C_6$-alkenyl, $C_3$-$C_6$-halogenoalkenyl, $C_3$-$C_6$-cycloalkyl, $C_5$-$C_6$-cycloalkenyl, or $C_3$-$C_6$-alkinyl; benzyl, which is unsubstituted or substituted in the benzene nucleus by chlorine or methyl; phenyl which is unsubstituted or mono- or di-substituted by $C_1$-$C_4$-alkyl, nitro, halogen or methoxy groups; the group $-N=C\overset{R^{14}}{\underset{R^{13}}{\diagdown}}$ or a cation of an inorganic or organic base;

$R^6$ is hydrogen, $C_1$-$C_4$-alkyl or phenyl; and $R^7$ is hydrogen, $C_1$-$C_6$-alkyl, which is unsubstituted or substituted by a hydroxyl group or a $C_1$-$C_3$ alkoxy group; $C_1$-$C_4$-alkylsulfonyl or halogeno-$C_1$-$C_4$-alkylsulfonyl; or $C_3$-alkenyl or $C_3$-alkinyl; or $R^6$ and $R^7$, together with the nitrogen atom, form pyrrolidino, piperidino, morpholino or piperazino; which is unsubstituted or substituted by up to two methyl groups;

$R^8$ is hydrogen, $C_1$-$C_6$-alkyl, phenyl, methylphenyl, halogenophenyl or a cation of an inorganic or organic base;

$R^9$ is hydrogen or $C_1$-$C_6$-alkyl;

$R^{10}$ is a radical having the meaning given for $R^5$, excluding hydrogen, alkylaminoalkyl or

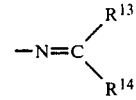

$R^{11}$ is hydrogen, $C_1$-$C_{12}$-alkyl, which is unsubstituted or mono-, di- or tri-substituted by halogen atoms or by a $C_1$-$C_4$-alkoxy, nitro, cyano or phenyl group, $C_3$-$C_6$-cycloalkyl, $C_3$-$C_6$-alkenyl, $C_3$-$C_6$-alkinyl, phenyl, which is unsubstituted or mono- or di-substituted by halogen, $C_1$-$C_4$-alkyl, trihalogenomethyl, nitro, $C_1$-$C_4$-alkoxy or cyano groups, amino, $C_1$-$C_4$-alkylamino, anilino, $C_1$-$C_4$-dialkylamino, $C_1$-$C_6$-alkylcarbonyl, trihalogenoacetyl, benzoyl, halogenobenzoyl, methylbenzoyl, phenylsulfonyl, halogenophenyl-sulfonyl or alkylphenylsulfonyl; and $R^{12}$ is a radical having the meaning given for $R^6$; or $R^{11}$ and $R^{12}$, together with the nitrogen atom, form pyrrolidino, piperidino, morpholino or piperazino which is unsubstituted or substituted by up to two methyl groups; and $R^{13}$ and $R^{14}$ independently of one another are hydrogen, $C_1$-$C_4$-alkyl, $C_1$-$C_4$-alkoxyalkyl, $C_3$-$C_6$-cycloalkyl or phenyl, or together with the carbon atom to which they are bonded are a $C_5$- or $C_6$-cycloalkyl group; or an optical isomer if $X \neq Y$, acid addition compound or N-oxide where A is N.

2. A compound as claimed in claim 1 which is

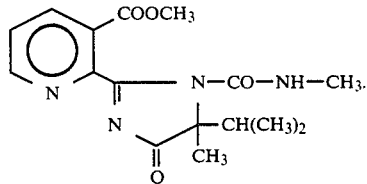

3. A compound as claimed in claim 1 which is

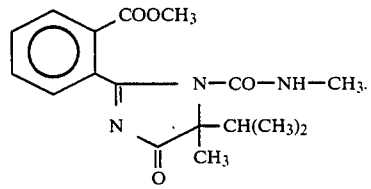

4. A compound as claimed in claim 1 which is

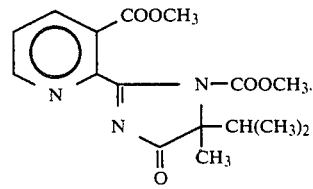

5. A compound as claimed in claim 1 which is

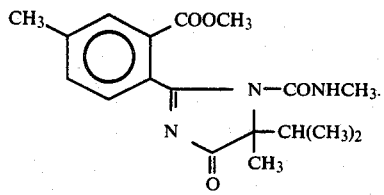

6. A compound as claimed in claim 1 which is

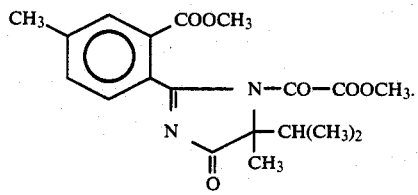

7. A compound as claimed in claim 1 which is

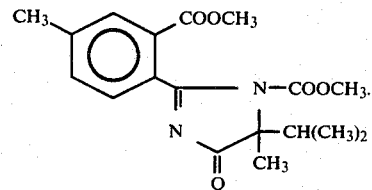

8. A compound as claimed in claim 1 which is

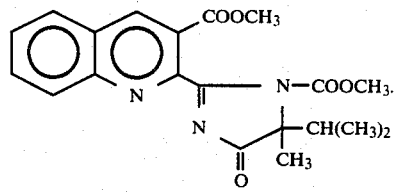

9. A herbicidal and plant growth-regulating agent, comprising an effective amount of a compound of the formula I of claim 1 in a carrier.

10. A method of combating undesirable plants, which comprises applying an effective amount of a compound of the formula I as claimed in claim 1 to an area where undesired plant growth occurs.

* * * * *